United States Patent [19]

Adachi et al.

[11] 4,339,435

[45] Jul. 13, 1982

[54] ANTI-TUMOR SUBSTANCE

[75] Inventors: Norihiko Adachi; Yoshikazu Fukai, both of Yokohama; Hisanori Kanayama, Machida, all of Japan

[73] Assignee: Japan Synthetic Rubber Co., Ltd., Tokyo, Japan

[21] Appl. No.: 123,482

[22] Filed: Feb. 21, 1980

[30] Foreign Application Priority Data

Feb. 22, 1979 [JP] Japan .................................. 54/19081

[51] Int. Cl.$^3$ ..................... A61K 35/00; A61K 31/70; C07G 3/00; C12P 19/04
[52] U.S. Cl. .................................. 424/115; 424/123; 424/180; 424/195; 435/101; 536/1.1
[58] Field of Search ............... 424/195, 180, 115, 123; 536/1; 435/101

[56] References Cited

U.S. PATENT DOCUMENTS 3,987,166  10/1976  Komatsu et al. .................... 424/180
4,138,479  2/1979  Truscheit et al. .................... 424/195

OTHER PUBLICATIONS

Saito et al., Agr. Biol. Chem., vol. 32, No. 10, pp. 1261–1269, (1968).

*Primary Examiner*—Donald B. Moyer
*Attorney, Agent, or Firm*—Oblon, Fisher, Spivak, McClelland & Maier

[57] ABSTRACT

A piece of internal tissue of the sclerotium of Poria cocos (Fr.) Wolf is transplanted into an artificial culture medium to subject it to pure culture of hyphae of said microorganism, thereby obtaining mycelia, and the thus obtained mycelia are extracted with at least one medium selected from the group consisting of water and water-soluble organic media. The resultant substance has an excellent ani-tumor activity and is low in toxicity.

14 Claims, No Drawings

ANTI-TUMOR SUBSTANCE

This invention relates to an anti-tumor substance obtained by extracting with water and/or a water-soluble organic medium the mycelia formed by artificial culture of a sclerotium of *Poria cocos* (Fr.) Wolf, and anti-tumor preparations using said substance.

Sclerotia of *Poria cocos* (Fr.) Wolf have long been used in the name of hoelen in the Chinese medicines. It has also been listed in the Japanese Pharamacopeia and is widely used as a medicinal substance having the diuretic and sedative activities.

The present inventors have found that a substance having a salient anti-tumor activity can be obtained by extracting with water and/or a water-soluble organic medium the mycelia obtained by pure culture of hyphae taken from hoelen.

*Poria cocos* (Fr.) Wolf used in this invention is mentioned in, for example, S. Udagawa et al., "Kinrui Zukan" (Microorganism Book) published by Kodansha, 1978 (see Note below), and an example thereof is a strain obtained by artificial incubation of a sclerotium of *Poria cocos* (Fr.) Wolf gathered in Kaga City, Ishikawa Prefecture, Japan in a culture medium consisting of 20 g of glucose, 5 g of yeast extract, 1 g of $KH_2PO_4$, 0.5 g of $MgSO_4.7H_2O$, 60 mg of $CaCl_2$, 4 mg of $ZnSO_4.7H_2O$, 5 mg of $MnSO_4.4-6H_2O$, 5 mg of ferric citrate, 20 g of agar powder and 1 liter of distilled water in the stationary state (solid) under an aerobic condition, said culture medium having a pH of 5.4 and having been sterilized at 121° C. for 15 min., which strain has been deposited in the Fermentation Research Institute, Agency of Industrial Science and Technology, Chiba, Japan and in the American Type Culture Collection under FERM-P No. 4766 and ATCC No. 20596, respectively.

Note:

*Poria cocos* (Fr.) Wolf

Form

Cultured hypha: is 2.5–6μ in width, colorless, a thin film, has septum, and is free from clamp connection.

Conidium: Not differentiated as conidium, but spherical cells of bud type are mononematos. The diameter is 2.5–6μ, and it is colorless and a thin film.

Fruit body: There is substantially nothing.

Basidium: is clavate to cylindrical, 2.5–30×4–6μ, and has 4 spores or 2 spores.

Basidiospore: is columnar, somewhat bent, sharp at the base end, colorless, smooth, 7–9×3–3.5μ.

Sclerotium: is spherical, ellipsoidal to indeterminate form, more than 30 cm in longer diameter, up to 5 kg in weight. The surface is redish brown to blackish redish brown, has large creases, and sometimes attached to root. The flesh is white to pink, and has dried cheese-like quality. In the outer layer, there are complicated hyphae and egg-shaped to irregular egg-shaped granules formed by expanding the end of the hyphae in admixture. In the inner layer, there are substantially no hyphae, and the inner layer is filled with the granules and plate-shaped mucilaginous materials.

Distribution, ecology: Distributed throughout Japan and in North America and China, and parasitic on the root of needle-leaf trees, such as pine, and fir, and in North America, also parasitic on the root of broad-leaved trees, to form sclerotia. The sclerotia are formed on the root 10 to 30 cm underground, and are often discovered in sands.

The *Poria cocos* (Fr.) Wolf used in this invention shows the form, distribution and ecology mentioned in the above Note, and the mycelia to be used in this invention are not limited to FERM-P 4766 or ATCC No. 20596.

According to this invention, there is provided an anti-tumor substance obtained by transplanting a piece of internal tissue of a sclerotium of *Poria cocos* (Fr.) Wolf into an artificial culture medium, subjecting it to pure culture of hyphae to obtain the corresponding mycelia and extracting these mycelia with at least one medium selected from the group consisting of water and water-soluble organic media.

Said pure culture may be accomplished with either a solid medium or a liquid medium, but liquid aeration culture is preferred because of easiness of control. This invention is described below referring to this liquid aeration culture as an example.

The culture medium may be prepared in the same way as in the case of ordinary culture of microorganisms by selecting the necessary components from carbon sources, nitrogen sources, inorganic salts, vitamins, etc., such as, for example, glucose, fructose, maltose, sucrose, starch, dextrin, blackstrap molasses, citric acid, fumaric acid, ammonium sulfate, ammonium chloride, ammonium phosphate, sodium nitrate, urea, amino acids, peptone, soybean whey, yeast extract, malt extract, meat extract, corn steep liquor, magnesium salts, phosphates, vitamins $B_1$, $B_6$ and C, etc.

The culture is usually carried out at a temperature of 10° to 33° C., preferably 15° to 30° C., for a period of 1 to 50 days under an aerobic condition. The culture products are subjected to a suitable treatment, such as filtration or centrifugation, to obtain mycelia.

The mycelia thus obtained are then suspended in at least one medium selected from the group consisting of water and water-soluble organic media and subjected to extraction at a temperature of 5° to 120° C. for a period of about 0.5 to 60 hours. The term "water-soluble organic media" as used herein refers to organic media which are soluble in water including alcohols, phenols, ethers, ketones, organic acids, and the like, and typical examples of such media are ethanol, phenol, trichloroacetic acid, dimethylsulfoxide, dimethylformamide, acetonitrile, dioxane, acetone, sulfolane, and ethylene glycol. In the extraction operation according to this invention, water and water-soluble organic media may be used either alone or in admixture of two or more. Preferably, water or a mixture containing water in a major amount is used.

In said extraction operation, a base, such as sodium hydroxide or potassium hydroxide, may be dissolved in the medium.

Upon completion of the extraction, the extract is treated by a suitable means, such as filtration or centrifugation, to get rid of the solid matter, thereby obtaining a clear solution.

This clear solution per se exhibits a strong anti-tumor activity. When this solution is concentrated by a rotary evaporator or other means and dried by means of a freeze-dryer or other like means, there is obtained a brown or pale brown powdery substance. This powdery substance also has an anti-tumor activity.

The powdery substance obtained from said extraction with water and/or a water-soluble organic medium is soluble in water, and the anti-tumor substance of this invention includes not only said powdery substance but also the extract per se obtained by said extraction with water and/or a water-soluble organic medium.

The anti-tumor substance of this invention can be formulated into various preparation forms, such as syrap, injection, drip, powder, granule, tablet, suppository, ointment, capsule, etc., according to the type of the tumor to be treated, the site in which tumor is generated, and the like. In the formulation of said preparation forms, there may be added suitable adjuvants and additives, if necessary, and any conventional manner for formulating preparations may be employed. It is also possible to mix other known anti-tumor agents as well as various kinds of medicines and nutrients.

The anti-tumor substance of this invention in the form of an anti-tumor preparation may be administered in various ways such as orally, intravenously, intraperitoneally, rectally, etc., depending on the type of the tumor to be treated, the site in which the tumor is generated, the preparation form, and the like.

In use of the anti-tumor substance of this invention in the form of an anti-tumor preparation, the dose thereof as calculated in terms of the amount of powdery substance is usually in the order of 1 to 1,000 mg/Kg/day in the case of intravenous or intraperitoneal administration and in the order of 10 to 10,000 mg/Kg/day in the case of oral administration form, though it may be varied depending on the conditions of patients, the preparation form, the administration way and the like.

An explanation is made below of the specific production of the anti-tumor substance of this invention, its anti-tumor activity and acute toxicity, and the specific preparation containing the anti-tumor substance referring to Examples.

(A) Production

Production Example 1

A piece of tissue was taken in a usual way from a sclerotium of *Poria cocos* (Fr.) Wolf gathered in Kaga City, Ishikawa Prefecture, Japan, and subjected to pure culture in a potato dextrose agar slant medium, and the culture product was preserved. The culture product was then transferred into three 300-ml Erlenmeyer flasks containing a GPY medium (see the note below) and subjected to stationary culture. One month later, the whole cultures were slurried by a homogenizer, and 200 ml thereof was subjected to aeration culture (aeration rate: 0.2 liter/liter of medium, 25° C.) in a 20-liter jar fermentor containing 10 liters of GPY medium for one week. Upon completion of the culture, the mycelium was separated by filtration and dried with warm air to obtain 38.0 g of dry mycelium.

The thus obtained dry mycelium (38.0 g) was pulverized by means of a coffee mill, put into a 5-liter flask provided with a reflux condenser together with 2 liters of distilled water, and then subjected to extraction at 95° C. for 5 hours.

The extract was filtered, and the filtrate was concentrated to 1 liter by a rotary evaporator and then freeze-dried to obtain 9.2 g of a brown powdery substance (hereinafter referred to as A-1).

| Note: | GPY medium | |
|---|---|---|
| | Glucose | 50 g |
| | Peptone | 2.5 g |
| | Yeast extract | 2.5 g |
| | KH$_2$PO$_4$ | 1.0 g |
| | MgSO$_4$ . 7H$_2$O | 0.5 g |

| -continued | |
|---|---|
| CaCl$_2$ . 2H$_2$O | 0.5 g |
| Distilled water | 1 liter |
| Minor constituent solution* | 20 ml |
| *Minor constituent solution | |
| FeCl$_2$ . 6H$_2$O | 0.5 g |
| MnCl$_2$ . 4H$_2$O | 0.36 g |
| ZnCl$_2$ | 0.2 g |
| CuSO$_4$ . 5H$_2$O | 0.05 g |
| Distilled water | 1 liter |

Production Example 2

Ten grams of the dry mycelia obtained in the same manner as in Production Example 1 was put into a 500-ml Erlenmeyer flask containing 200 ml of 1 N sodium hydroxide solution and subjected to extraction at room temperature for 6 hours.

After the extraction, the extract was filtered, and the filtrate was dialyzed with a cellulose tube and the inner solution was concentrated and freeze-dried to obtain 4.5 g of a pale brown powdery substance (hereinafter referred to as A-2).

Production Example 3

The same procedure as in Production Example 2 was repeated, except that 200 ml of a 45% phenol solution was substituted for the sodium hydroxide and extraction was effected in a flask provided with a reflux condenser at 60° C. for 6 hours with stirring. The extract was filtered and dialyzed in the same manner as in Production Example 2, and the inner solution was concentrated and freeze-dried to obtain 1.1 g of a brown powdery substance (hereinafter referred to as A-3).

Production Example 4

In a usual way, a piece of tissue was take from the same sclerotium of *Poria cocos* (Fr.) Wolf as in Production Example 1, and subjected to pure culture in a culture medium consisting of 20 g of glucose, 5 g of yeast extract, 1 g of KH$_2$PO$_4$, 0.5 g of MgSO$_4$.7H$_2$O, 60 mg of CaCl$_2$, 4 mg of ZnSO$_4$.7H$_2$O, 5 mg of MnSO$_4$.4-6H$_2$O, 5 mg of ferric citrate, 20 g of agar powder and 1 liter of distilled water in the stationary state (solid) under an aerobic condition, said culture medium having a pH of 5.4 and having been sterillized at 121° C. for 15 min. The culture product obtained was subjected to the same operation as in Production Example 1 using the same GPY medium as in Production Example 1, to obtain 39.0 g of dry mycelium. The dry mycelium obtained (10 g) was put into a 500-ml Erlenmyer flask containing 200 ml of 50% aqueous ethanol and then subjected to extraction at 60° C. for 10 hours with stirring, after which the extract was filtered, and the filtrate was then dialyzed with a cellulose tube. The inner solution was concentrated and freeze-dried to obtain 300 mg of a pale brown powdery substance (hereinafter referred to as A-4).

Production Example 5

The same procedure as in Production Example 4 was repeated, except that a medium as shown in Table 1 was substituted for the 50% aqueous ethanol, to obtain a brown powdery substance as shown in Table 1.

TABLE 1

| Medium | Yield of powdery substance | Sample No. |
| --- | --- | --- |
| 50% Aqueous dioxane | 280 mg | A-5 |
| 50% Aqueous acetonitrile | 440 mg | A-6 |
| 50% Aqueous acetone | 150 mg | A-7 |
| 50% Aqueous sulfolane | 400 mg | A-8 |

Production Example 6

The same procedure as in Production Example 4 was repeated, except that a medium as shown in Table 2 was substituted for the 50% aqueous ethanol and the extraction was effected at room temperature, to obtain a brown powdery substance as shown in Table 2.

TABLE 2

| Medium | Yield of powdery substance | Sample No. |
| --- | --- | --- |
| 50% Aqueous ethylene glycol | 380 mg | A-9 |
| 50% Aqueous trichloroacetic acid | 850 mg | A-10 |
| Ethylene glycol | 200 mg | A-11 |

(B) Anti-tumor activity

Measurement Example 1

Ascites tumor cells of Sarcoma-180, which had been subjected to successive cultivation at a rate of once a week, were inoculated subcutaneously into the right inguinal regions of 5-week-old male ICR-JCL mice at a rate of $10^6$ cells/mouse, and after the lapse of 24 hours from said inoculation, the Sample A-1 dissolved in physiological salt solution was intraperitoneally administered to said mice at a dose of 100 mg/Kg once a day for a total period of 10 days. The mice were anatomized 30 days after said tumor inoculation and the tumors were enucleated. The weight of each enucleated tumor was measured and compared with that of the simultaneously assayed control group of mice, to which the physiological salt solution alone was administered after the tumor inoculation, and the tumor inhibition ratio (IR) was calculated from the following equation:

$$IR = (1 - T/C) \times 100\%$$

where
T: average tumor weight (g) of the A-1 administered group.
C: average tumor weight (g) of the control group. The results are shown in Table 3, from which the effect of A-1 is evident.

TABLE 3

| | Number of mice tested | Number of mice in which tumors were completely recessed | Average tumor weight | IR |
| --- | --- | --- | --- | --- |
| A-1 | 10 | 6 | 0.6 g | 92% |
| Control* | 10 | 0 | 7.4 g | — |

Note:
*Physiological salt solution alone was given after tumor inoculation.

Measurement Example 2

Samples A-2 and A-3 were assayed in the same manner as in Measurement Example 1, except that the dose was changed to 200 mg/Kg/day. The results are shown in Table 4.

TABLE 4

| | Number of mice tested | Number of mice in which tumors were completely recessed | Average tumor weight | IR |
| --- | --- | --- | --- | --- |
| A-2 | 10 | 3 | 0.4 g | 93% |
| A-3 | 10 | 0 | 1.7 g | 72% |
| Control* | 10 | 0 | 6.1 g | — |

Note:
*Same as in Table 3.

Measurement Example 3

The same procedure as in Measurement Example 1 was repeated, except that distilled water was substituted for the physiological salt solution, and Sample A-1 was orally administered at a dose of 1,000 mg/Kg/day, to obtain the results shown in Table 5.

TABLE 5

| | Number of mice tested | Average tumor weight | IR |
| --- | --- | --- | --- |
| A-1 | 10 | 2.2 g | 61% |
| Control* | 10 | 5.7 g | — |

Note:
*Distilled water alone was given after tumor inoculation

Measurement Example 4

In the same manner as in Measurement Example 1, Samples A-5 to A-10 were administered to male ICR-JCL mice, and the results obtained are shown in Table 6.

TABLE 6

| | Number of mice tested | Number of mice in which tumors were completely recessed | Average tumor weight | IR |
| --- | --- | --- | --- | --- |
| A-4 | 10 | 0/10 | 3.1 g | 60% |
| A-5 | 10 | 0/10 | 3.3 g | 58% |
| A-6 | 10 | 0/10 | 3.7 g | 52% |
| A-7 | 10 | 0/10 | 4.4 g | 44% |
| A-8 | 10 | 0/10 | 3.3 g | 58% |
| A-9 | 10 | 1/10 | 1.2 g | 85% |
| A-10 | 10 | 0/10 | 3.1 g | 60% |
| A-11 | 10 | 0/10 | 3.9 g | 50% |
| Control* | 10 | 0/10 | 7.8 g | — |

Note:
*Same as in Table 3.

(C) Acute Toxicity Test

Test Example 1

Sample A-1 dissolved in a physiological salt solution was administered intraperitoneally at 5,000 mg/Kg to ten 5-week-old male ICR-JCL mice (average weight: 28.5 g), and the mice were observed for seven days.

The mice were unfed for 18 hours before administration of A-1. Hairs rose slightly and motion inhibition was observed immediately after the administration of Sample A-1, but they were recovered soon. Thereafter, the weight increase was normal and no change was observed in other respects.

Test Example 2

The same procedure as in Test Example 1 was repeated, except that the sample was administered orally (20,000 mg/Kg) instead of the intraperitoneal administration. There was observed slight rise of hairs as in Test Example 1, but the hairs were soon recovered. Further, the weight increase was normal and no change was observed in other respects as in Test Example 1.

(D) Preparations

Preparation Example 1

One gram of Sample A-1 was dissolved in 50 ml of distilled water (or physiological salt solution) for injection and then filtered, after which the filtrate was put into an ampule, heat-sealed and then sterilized by heating in a usual way.

Preparation Example 2

Sample A-1 was finely powdered with care so that it did not absorb moisture and the powder was screened through a 120-mesh wire gauze, and the powder which passed through the wire gauze was packed and sealed in aluminum-laminated polyethylene pouches in a proportion of 1 g per pouch.

Preparation Example 3

A mixture of 20% by weight of Sample A-1, 75% by weight of lactose and 5% by weight of hydrogenation product of rapeseed oil having a melting point of 60° C. was sufficiently stirred and formed into tablets each having a weight of 250 mg by means of a tablet machine.

What is claimed is:

1. A substance having an anti-tumor activity obtained by transplanting a part of the internal tissue of a sclerotium of *Poria cocos* (Fr.) Wolf into an a culture medium, subjecting it to pure culturing of hyphae of said microorganism to obtain mycelia thereof, separating said mycelia and extracting said mycelia with at least one medium selected from the group consisting of water and water-soluble organic solvent.

2. The substance according to claim 1, wherein the *Poria cocos* (Fr.) Wolf is the strain of ATCC No. 20596.

3. The substance according to claim 1, wherein the culture is carried out at a temperature of 10° to 33° C. for a period of 1 to 50 days under an aerobic condition.

4. The substance according to claim 1, 2 or 3, wherein the extraction is performed at a temperature of 5° to 120° C. for a period of 0.5 to 60 hours.

5. The substance according to claim 4, wherein the extraction solvent is water, or a mixture of a major amount of water and a minor amount of a water-soluble organic solvent.

6. The substance according to claim 1, 2 or 3, wherein the water-soluble organic solvent is an alcohol, a phenol, an ether, a ketone or an organic acid.

7. The substance according to claim 1, 2 or 3, wherein the water-soluble organic solvent is ethanol, phenol, trichloroacetic acid, dimethylsulfoxide, dimethylformamide, acetonitrile, dioxane, acetone, sulfolane, or ethylene glycol.

8. The substance according to claim 1, 2 or 3, wherein the extraction solvent is water or a mixture of a major amount of water and a minor amount of a water-soluble organic solvent.

9. The substance according to claim 1, 2 or 3, wherein the extraction solvent is water.

10. A method for preparing a substance having an anti-tumor activity, comprising transplanting a part of the internal tissue of a sclerotium of *Poria cocos* (Fr.) Wolf into a culture medium, subjecting it to pure culturing of hyphae of said microorganism to obtain mycelia thereof, separating said mycelia, and extracting said mycelia with at least one solvent selected from the group consisting of water and water-soluble organic solvents.

11. The method according to claim 10, wherein the culturing is carried out at a temperature of 10° to 33° C. for a period of 1 to 50 days under an aerobic condition.

12. The method according to claim 10, wherein the extraction is performed at a temperature of 5° to 120° C. for a period of 0.5 to 60 hours.

13. The process according to claim 10, wherein the *Poria cocos* (Fr.) Wolf is the strain ATCC No. 20596.

14. The process according to claim 10, wherein the solvent medium contains a basic substance selected from the group consisting of sodium hydroxide or potassium hydroxide.

* * * * *